(12) United States Patent
Jezek et al.

(10) Patent No.: US 9,345,804 B2
(45) Date of Patent: May 24, 2016

(54) S-NITROSOTHIOL-GENERATING SKIN DRESSINGS

(71) Applicant: Insense Limited, Bedford (GB)

(72) Inventors: Jan Jezek, Stanwick (GB); Lynne Patricia Watson, Wootton (GB)

(73) Assignee: Insense Limited, Bedford (GB)

( * ) Notice: Subject to any disclaimer, the term of this patent is extended or adjusted under 35 U.S.C. 154(b) by 48 days.

(21) Appl. No.: 14/511,543

(22) Filed: Oct. 10, 2014

(65) Prior Publication Data

US 2015/0086651 A1     Mar. 26, 2015

Related U.S. Application Data

(63) Continuation-in-part of application No. 12/670,675, filed as application No. PCT/GB2008/050565 on Jul. 14, 2008, now abandoned.

(30) Foreign Application Priority Data

Aug. 9, 2007 (GB) .................................. 0715554.2

(51) Int. Cl.

| | |
|---|---|
| *A61K 9/70* | (2006.01) |
| *A61K 31/095* | (2006.01) |
| *A61K 33/26* | (2006.01) |
| *A61K 33/30* | (2006.01) |
| *A61K 33/34* | (2006.01) |
| *A61L 15/00* | (2006.01) |
| *A61L 26/00* | (2006.01) |
| *A61K 33/00* | (2006.01) |
| *A61L 15/18* | (2006.01) |
| *A61L 15/24* | (2006.01) |
| *A61L 15/44* | (2006.01) |
| *A61K 45/06* | (2006.01) |
| *A61K 33/06* | (2006.01) |
| *A61K 33/32* | (2006.01) |
| *A61K 8/46* | (2006.01) |
| *A61K 8/02* | (2006.01) |
| *A61K 8/19* | (2006.01) |

(52) U.S. Cl.
CPC ............ *A61L 26/0066* (2013.01); *A61K 8/0208* (2013.01); *A61K 8/19* (2013.01); *A61K 8/46* (2013.01); *A61K 31/095* (2013.01); *A61K 33/00* (2013.01); *A61K 33/06* (2013.01); *A61K 33/26* (2013.01); *A61K 33/30* (2013.01); *A61K 33/32* (2013.01); *A61K 33/34* (2013.01); *A61K 45/06* (2013.01); *A61L 15/18* (2013.01); *A61L 15/24* (2013.01); *A61L 15/44* (2013.01); *A61L 26/0004* (2013.01); *A61L 26/0014* (2013.01); *A61L 2300/114* (2013.01); *A61L 2300/216* (2013.01)

(58) Field of Classification Search
None
See application file for complete search history.

(56) References Cited

U.S. PATENT DOCUMENTS

| | | |
|---|---|---|
| 5,648,101 A | 7/1997 | Tawashi |
| 2002/0115559 A1 | 8/2002 | Batchelor et al. |
| 2003/0045865 A1 | 3/2003 | Knapp |
| 2005/0181026 A1 | 8/2005 | Davis et al. |

FOREIGN PATENT DOCUMENTS

| | | |
|---|---|---|
| WO | WO 01/96422 | 12/2001 |
| WO | WO 03/017989 | 3/2003 |
| WO | WO 03/090800 | 11/2003 |
| WO | WO 2005/094913 | 10/2005 |
| WO | WO 2006/095193 | 9/2006 |

OTHER PUBLICATIONS

Glucose Oxidase fact sheet; Roche; Jan. 2007.
International Search Report for corresponding International Application No. PCT/GB2008/050565, dated Oct. 16, 2009.
UK Intellectual Property Office Search Report for GB0715554.2, dated Dec. 6, 2007.

*Primary Examiner* — Kevin S Orwig
(74) *Attorney, Agent, or Firm* — Dascenzo Intellectual Property Law, P.C.

(57) ABSTRACT

The present disclosure relates to a skin dressing adapted, on activation, to generate one or more S-nitrosothiols by reaction between a thiol and a nitrite salt in the skin dressing for delivery of nitric oxide to a body site. The skin dressing comprises a source of $Cu^{2+}$, $Zn^{2+}$ and/or $Fe^{2+}$ ions.

15 Claims, 3 Drawing Sheets

S-NITROSOTHIOL-GENERATING SKIN DRESSINGS

RELATED APPLICATIONS

This application is a continuation-in-part and claims priority under 35 U.S.C. §120 to U.S. patent application Ser. No. 12/670,675, which was filed on Jan. 26, 2010, and which claims priority from PCT Patent Application No. PCT/GB2008/050565, which was filed on Jul. 14, 2008. PCT Patent Application No. PCT/GB/2008/050565 claims priority from United Kingdom Patent Application No. 0715554.2, which was filed on Aug. 9, 2007. The complete disclosures of the above-identified patent applications are hereby incorporated by reference.

FIELD

The present disclosure relates to skin dressings for application to a part of a human or animal body for treatment of skin (for therapeutic or cosmetic purposes).

BACKGROUND

Nitric oxide has a multitude of effects in living tissues. The mechanism of these effects is nearly always based on interaction of nitric oxide either with a metal component (typically iron) or with thiol groups of key enzymes and other proteins. Depending on the particular enzyme, such interaction can lead to either activation or inhibition of the protein. An example of an effect based on the activation of an enzyme is that of vasodilatation: nitric oxide binds to the haem iron of the enzyme guanylate cyclase, which results in conformational change exposing the catalytic site of the enzyme. This leads to catalytic conversion of GTP to cGMP. This conversion initiates the whole cascade of reactions leading to protein phosphorylation and muscle relaxation (vasodilatation). Other effects based on activation of enzymes or growth factors by nitric oxide include stimulation of cell division (proliferation) and cell maturation, stimulation of cell differentiation and formation of cell receptors, neovascularisation, formation of fibroblasts in the wound and thereby enhancement of collagen formation, etc.

Topical delivery of nitric oxide can be a very useful feature in various therapeutic or cosmetic applications including wound healing, treatment of skin or nail infections, sexual dysfunction etc.

Under normal conditions, nitric oxide (NO) is a short-lived, unstable gaseous substance. Its instability is due to the unpaired electron of nitrogen. It is therefore beneficial to deliver nitric oxide topically in the form of a nitric oxide donor which diffuses into the body site and releases nitric oxide, either spontaneously or on activation. Particularly useful nitric oxide donors are nitrosothiols. Nitrosothiols are donors of nitric oxide which can be released by their spontaneous decomposition:

The rate of decomposition varies considerably depending on the side chain of the thiol. For example, whilst nitrosocysteine can be almost totally decomposed within minutes under normal conditions, it takes hours/days to achieve almost complete decomposition of nitrosoglycerol. The decomposition can be accelerated markedly in the presence of $Cu^{2+}$ and $Hg^{2+}$. Nitrosothiols are also able to donate nitric oxide directly onto another thiol group. This process, which is called trans-nitrosation, is quite common in vivo:

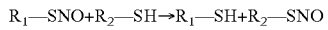

Nitrosothiols can be produced by reaction between thiols and nitrite in an acidic environment. The reaction mechanism involves formation of nitrosonium cation ($NO^+$) which, in turn, reacts with a thiol to produce corresponding nitrosothiol:

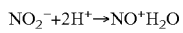

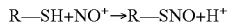

S-nitrosothiols can thus be produced conveniently by mixing a thiol (e.g. thioglycerol) with a source of nitrite (e.g. potassium nitrite) in acidic solution. The reaction proceeds at pH<6, the rate of the reaction increasing with the acidity of the solution:

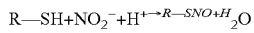

WO2006/095193 discloses a skin dressing adapted, on activation, to release one or more S-nitrosothiols. The dressing comprises one or more components containing a source of nitrite, a source of thiol and a source of protons.

It is a well known fact that the rate of the nitrosothiol generation can be controlled by pH. In principle, the rate increases with increasing acidity of the formulation containing a source of nitrite and a thiol. However, whilst it is possible to ensure such rapid generation of nitrosothiols simply by adjusting pH, the acidity required may prevent applicability of such formulation (for example when applied onto intact or wounded skin).

Whilst some applications may require only a slow rate of nitrosothiol generation, there are other applications that benefit from a rapid burst of nitrosothiols. It is possible to ensure such rapid generation of nitrosothiols simply by adjusting pH, but the acidity required may prevent applicability of such formulation (for example when applied onto intact or wounded skin).

SUMMARY

The present disclosure relates to a skin dressing adapted, on activation, to generate one or more S-nitrosothiols by reaction between a thiol and a nitrite salt in the skin dressing for delivery of nitric oxide to a body site. The skin dressing comprises a source of $Cu^{2+}$, $Zn^{2+}$ and/or $Fe^{2+}$ ions.

DESCRIPTION

Figure 1:
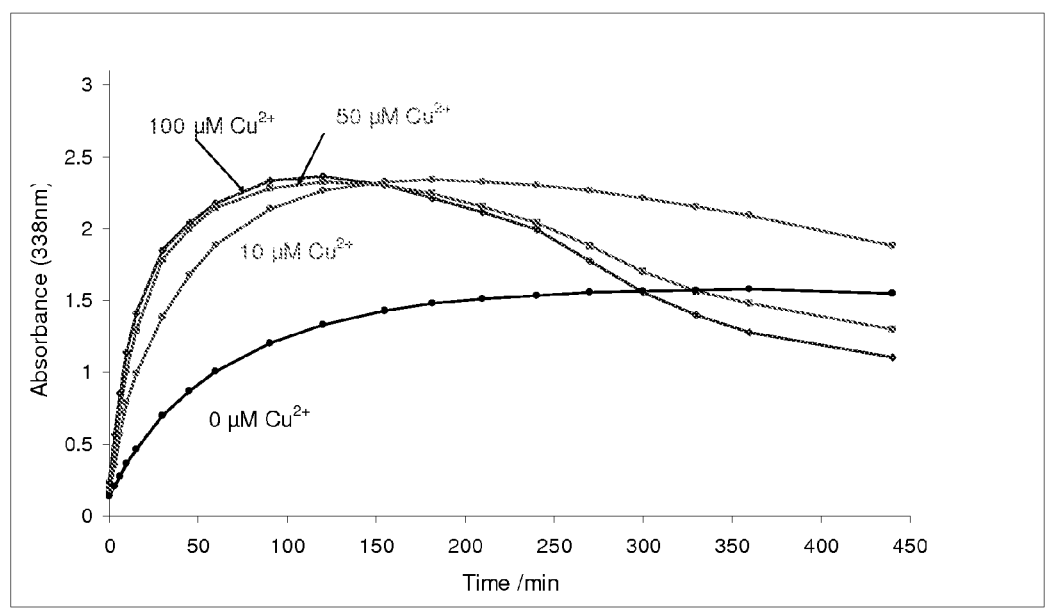
FIG. 1 is a graph of absorbance (338 nm) versus time (in minutes) showing the effect of cupric cations on the rate of nitrosylation of 1-thioglycerol at pH 4.0. The absorbance (338 nm) is directly proportional to the concentration of S-nitroso-1-thioglycerol in the solution.

The present disclosure relates to skin dressings for application to a part of a human or animal body for treatment of skin (for therapeutic or cosmetic purposes), and relates particularly (but not exclusively) to wound dressings for treatment of compromised skin, particularly skin lesions, i.e. any interruption in the surface of the skin, whether caused by injury or disease, including skin ulcers, burns, cuts, punctures, lacerations, blunt traumas, acne lesions, boils etc. The term "skin dressing" covers dressings such as patches, plasters, bandages and gauze etc. for use in connection with transdermal delivery of agents. The term also includes material in amorphous or liquid form. The term covers dressings for application to body surfaces generally, including internal and external tissues, particularly the skin including the scalp. The present disclosure is based on the beneficial properties of nitric oxide (NO).

The disclosure is based on the surprising finding that the presence of cations of transition metals, such as $Cu^{2+}$, $Zn^{2+}$ or $Fe^{2+}$, preferably $Cu^{2+}$, can increase the rate of nitrosothiol production in a system containing a source of nitrite and a thiol. This is achieved without any changes of the pH of the formulation. This effect provides an alternative control over the rate of nitrosothiol generation and allows a more rapid nitrosothiol generation to be achieved at milder pH, which is less irritating and harmful to skin.

Whilst the effect of two metal cations ($Hg^{2+}$ and $Cu^{2+}$) on the rate of nitrosothiol decomposition has been well established for several decades, the use of these metal cations would generally decrease the availability of nitrosothiols due to the rapid decomposition. The use of transition metals to increase the rate of nitrosothiol production was not previously considered.

It will be appreciated that nitrite is a compound with a $pK_a$ of 3.4 (at 25° C.). Thus, nitrite can act as a buffer in the system, capable of maintaining pH in the range of from 3 to 4.

After activating the dressing, e.g. by bringing two components together, at a skin site (e.g. a wound site), the pH will be such that S-nitrosothiols begin to be generated. During this reaction, nitrite will help to maintain an acidic environment. However, its buffering capacity will reduce as the reaction proceeds.

Preferably there are no additional buffers with a $pK_a$ of less than 5 (e.g. less than 4.5, less than 4, from 1 to 4, from 1 to 4.5, and/or from 1 to 5) in the dressing so that the pH of the dressing rises as the reaction proceeds, increasing the pH from an acidic value (e.g. below 5, e.g. from 3 to 4) to a more neutral value (e.g. above 5, e.g. from 6 to 7).

Although the rise in pH will reduce and eventually may stop production of S-nitrosothiols, the presence of a source of $Cu^{2+}$, $Zn^{2+}$ and/or $Fe^{2+}$ ions, particularly $Cu^{2+}$, accelerates production of S-nitrosothiols, allowing production to continue at higher pH values (e.g. at a pH of above about 3, above about 4, above about 5 or above about 6).

For example, if rapid generation of nitric oxide is required in order to achieve a localized vasodilatation and consequent increase of blood flow then the pH of the formulation immediately after activation must be very low so that the nitrosylation of thiol proceeds very readily. However, in the presence of cations of transition metals the same rapid rate of thiol nitrosylation can be achieved at a milder pH (e.g. at a pH more neutral than about 3, about 4, about 5 or about 6).

The thiol may be preferably selected from the group consisting of 1-thioglycerol, 1-thioglucose, methyl- or ethyl-ester of cysteine.

Other suitable thiols include glutathione (L-glutathione, as this is the physiologically important version), cysteine, N-acetylcysteine, mercaptoethylamine, and 3-mercaptopropanoic acid.

The one or more S-nitrosothiols are generated by reacting together reagents in the dressing.

The dressing includes a nitrite and a thiol, e.g. 1-thioglycerol that react together in the dressing on activation to generate and release S-nitrosothiol. Nitrites generally are inorganic nitrite salts (or a combination of inorganic nitrite salts) such as sodium nitrite, potassium nitrite, calcium nitrite, magnesium nitrite, and manganese nitrite.

The reagents may be suitably provided in separate components of the dressing that are kept apart prior to use. The dressing may be said to be in a separated state or a storage state while the dressing components are separated. To activate the dressing, and to place the dressing into an activated state, the two dressing components are brought into contact (in the presence of a source of water and protons, if required), resulting in production in the dressing of the S-nitrosothiol that is then typically released from the dressing. Preferably, the two dressing components are packaged separately. Alternatively, they can be brought into contact and packaged together in a sealed container so that they are ready for use as a one component system when unpackaged. The dressing may comprise at least two components, with one component comprising the thiol and another component comprising the nitrite. Any or all of the components may comprise (optionally substantially exclusively comprise) the source of $Cu^{2+}$, $Zn^{2+}$ and/or $Fe^{2+}$ ions. Additionally or alternatively, the source of ions may be comprised in a component of the skin dressing without any thiol or nitrite.

In this at least two-component arrangement, typically a first component (e.g. the nitrite-containing component) is acidic, for example, having a pH in the range of from 2 to 5, from 3 to 5, and/or from 3 to 4. A second component (e.g. the thiol-containing component) may have a pH in the range of from 5 to 12, e.g. from 6 to 11 and/or from 7 to 10. A small amount of buffer with a $pK_a$ in the range of from 7 to 12 is optionally present in the second component.

The first component additionally may comprise a buffer with a $pK_a$ of from 4.5 to 7.0, e.g. from 5 to 6, and/or about 5.5. As discussed above, the first component may be acidic with, for example, a pH of from 2 to 5. At this pH, a very high proportion of the buffer will be present in protonated form and can thus serve as a useful source (or reservoir) of protons. Hence, the pH of the first component may be lower than the $pK_a$ of the buffer.

Since the buffering capacity of this buffer is minimal at pH between about 3 to 4, nitrite will be a dominant buffer in the composition following activation. As the conversion of nitrite to S-nitrosothiol proceeds, accompanied by consumption of protons, the buffering capacity of nitrite will diminish and pH will increase. The buffering contribution of the source of protons buffer (with e.g. $pK_a$ about 5.5) will be minimal in the initial stages, but it will prevent the pH from rising too sharply above 4.5, where the conversion of nitrite to S-nitrosothiol is rather inefficient. The pH will only reach those levels if most nitrite is converted, at which point low pH is no longer required as the build-up of nitric oxide has been achieved.

Thus, there is a co-operation between nitrite ($pK_a$ 3.4) and the source of protons buffer ($pK_a$ about 5.5) in terms of proton exchange, ensuring an efficient conversion of nitrite whilst maintaining a mild pH environment.

Suitable amounts of the reagents can be readily determined to achieve the desired rate and yield of production of one or more S-nitrosothiols. In general, amounts of each reagent in the range 0.1%-5% (w/w), based on the dressing, are likely to be appropriate.

The or each dressing component may be in the form of a layer, e.g. in the form of a sheet, slab or film, that may be produced from an amorphous material, not having any fixed form or shape, that can be deformed and shaped in three dimensions, including being squeezed through a nozzle.

The or each dressing component conveniently comprises a carrier or support, typically in the form of a polymeric matrix. The or each component of the system can be in the form of liquid, amorphous gel or in the form of a layer e.g. in the form of a sheet, slab or dry film. A particularly convenient support comprises a polymer based on polyacrylic acid which contains dissociable groups with $pK_a$ between 5 to 6.

The carrier or support conveniently comprises a hydrated hydrogel. A hydrated hydrogel means one or more water-based or aqueous gels, in hydrated form. A hydrated hydrogel thus includes a source of water, for activation of the dressing. A hydrated hydrogel can also act to absorb water and other materials exuded from a wound site, enabling the dressing to perform a valuable and useful function by removing such materials from a wound site. The hydrated hydrogel also provides a source of moisture that can act in use to maintain a wound site moist, aiding healing.

Suitable hydrated hydrogels are disclosed in WO 03/090800. The hydrated hydrogel conveniently comprises hydrophilic polymer material. Suitable hydrophilic polymer materials include polyacrylates and methacrylates, e.g. as supplied by First Water Ltd in the form of proprietary hydrogels, including poly 2-acrylamido-2-methylpropane sulphonic acid (poly-AMPS) and/or salts thereof (e.g. as described in WO 01/96422), polysaccharides e.g. polysaccharide gums particularly xanthan gum (e.g. available under the Trade Mark Keltrol), various sugars, polycarboxylic acids (e.g. available under the Trade Mark Gantrez AN-169 BF from ISP Europe), poly(methyl vinyl ether co-maleic anhydride) (e.g. available under the Trade Mark Gantrez AN 139, having a molecular weight in the range 20,000 to 40,000), polyvinyl pyrrolidone (e.g. in the form of commercially available grades known as PVP K-30 and PVP K-90), polyethylene oxide (e.g. available under the Trade Mark Polyox WSR-301), polyvinyl alcohol (e.g. available under the Trade Mark Elvanol), cross-linked polyacrylic polymer (e.g. available under the Trade Mark Carbopol EZ-1), celluloses and modified celluloses including hydroxypropyl cellulose (e.g. available under the Trade Mark Klucel EEF), sodium carboxymethyl cellulose (e.g. available under the Trade Mark Cellulose Gum 7LF) and hydroxyethyl cellulose (e.g. available under the Trade Mark Natrosol 250 LR).

Mixtures of hydrophilic polymer materials may be used in a gel.

In a hydrated hydrogel of hydrophilic polymer material, the hydrophilic polymer material is desirably present at a concentration of at least 1%, preferably at least 2%, more preferably at least 5%, yet more preferably at least 10%, or at least 20%, desirably at least 25% and even more desirably at least 30% by weight based on the total weight of the gel. Even higher amounts, up to about 40% by weight based on the total weight of the gel, may be used.

Good results have been obtained with use of a hydrated hydrogel of poly-AMPS and/or salts thereof in an amount of about 30% by weight of the total weight of the gel.

The hydrated hydrogel material is typically in the form of a solid layer, sheet or film of material that is typically cross-linked, and that may incorporate a mechanical reinforcing structure. The size and shape of the layer, sheet or film can be selected to suit the intended use of the dressing. Thicknesses in the range 0.05 to 5 mm, preferably 0.5 to 3 mm are particularly suitable.

Alternatively, the hydrated hydrogel may be in the form of an amorphous gel, not having a fixed form or shape, that can be deformed and shaped in three dimensions, including being squeezed through a nozzle. Amorphous gels are typically not cross-linked or have low levels of cross-linking. A shear-thinning (thixotropic) amorphous gel may be used. Such a gel is liquid when subjected to shear stress (e.g. when being poured or squeezed through a nozzle) but set when static. Thus the gel may be in the form of a pourable or squeezable component that may be dispensed, e.g. from a compressible tube or a syringe-like dispenser, comprising a piston and cylinder, typically with a nozzle of about 3 mm diameter. Amorphous gels allow efficient mixing of the two-component system. Such a gel may be applied in the form of a surface layer, or into a wound cavity as a fully conformable gel that fills the available space and contacts the wound surface.

A typical example of an amorphous gel formulation is: 15% w/w AMPS (sodium salt), 0.19% polyethylene glycol diacrylate and 0.01% hydroxycyclohexyl phenyl ketone, with the volume made up to 100% with analytical grade DI water. The reagents are thoroughly mixed and dissolved, then polymerized for between 30-60 seconds, using a UV-A lamp delivering approximately 100 mW/cm$^2$, to form the required hydrogel. This may be contained in plastic syringes from which the amorphous gel may then be dispensed from a syringe to a target site, as a surface layer or to fill a cavity.

The components of the dressing can also be in the dry form. Examples of suitable dry support polymer materials comprise polyvinylalcohol (PVA), alginate or carboxymethylcellulose. The stability of the active substances, especially thiols, will generally be better in the dry form.

In one embodiment the invention comprises a first component comprising a layer of hydrated hydrogel, preferably poly-AMPS and/or salts thereof, containing a source of nitrite, e.g. potassium nitrite, and a second component comprising a dry polymeric matrix, preferably dried PVA, containing a thiol, e.g. 1-thioglycerol. The first component may be used in contact with the skin, as the hydrated hydrogel has beneficial properties for skin contact, as discussed above, with the second component being placed on top of the first component. Alternatively, the first component may comprise the hydrated hydrogel and the thiol, while the second component may comprise the dry polymeric matrix and the source of nitrite. When the two components are brought into contact, this has the effect of activating the dressing. The water in the hydrated hydrogel of the first component functions to provide a suitable aqueous environment allowing generation of S-nitrosothiol.

In another embodiment, the dressing comprises two components which are amorphous. The components can be in the form of e.g. a gel, semi-solid, paste, cream, emulsion, lotion, thickened solution, or liquid e.g. an aqueous solution. Amorphous components may be thixotropic, exhibiting shear thinning. Hydrated hydrogels may be conveniently employed, as discussed above. In embodiments of this type, each component preferably contains a reagent which, when brought together, activate to release one or more S-nitrosothiols. Preferably one component contains a nitrite and the other contains a thiol. Alternatively the nitrite and thiol could be kept together at a high enough pH to prevent reaction thereof, e.g. at a pH above 7, the second component containing a source of acidity. Another possibility is that one component contains anhydrous S-nitrosothiol and the second component contains water.

The two amorphous components are kept separate until it is desired to apply the dressing to a body surface. Conveniently they are packaged in a container having a nozzle, through which the amorphous components can be delivered. Preferably, the two components are packaged in a two-compartment dispenser, preferably being operable to deliver both components simultaneously. The two-compartment dispenser may be configured to operate by hand, for example, a hand pump, a finger pump, and the like that may be operated by pressing with a finger. The two components can also be brought into contact and packaged together in a sealed container so that they are ready for use as a one component system when unpackaged.

In yet another embodiment the dressing comprises two dry components. Examples of suitable dry support polymer materials comprise polyvinylalcohol (PVA), alginate or carboxymethylcellulose. The two components can be kept separate during storage and activated by bringing them together and adding moisture. Alternatively, they can be kept together during storage and be activated by adding moisture (e.g. moisture from the wound site).

Preferred embodiments comprise two dressing components, one containing nitrite and the other containing thiol, e.g. glutathione. The two components can take a wide variety of material forms, as discussed above. However, the following examples of combinations are currently preferred:

| Nitrite component | Thiol component |
|---|---|
| Water | Dry film or sheet |
| Water | Dry film or sheet with glycerol humectant |
| Viscous aqueous solution | Dry film or sheet |
| Viscous aqueous solution | Suspension in glycerol |
| Water | Suspension in propylene glycol |
| Amorphous gel | Water |
| Water | Water |
| Amorphous gel | Amorphous gel |
| Water | Sheet hydrogel |
| Sheet hydrogel | Water |
| High water content sheet hydrogel | High water content sheet hydrogel |
| Dry film or sheet | Dry film or sheet |

The dressing optionally includes, or is used with, a skin contact layer, preferably comprising a hydrated hydrogel of poly-AMPS and/or salts thereof, as mentioned above.

The dressing optionally includes, or is used with, a covering or outer layer for adhering the dressing to the skin of a human or animal in a known manner. Dressings in accordance with the invention can be manufactured in a range of different sizes and shapes for treatment of areas of skin, e.g. wounds of different sizes and shapes. Appropriate amounts of reagents for a particular dressing can be readily determined by experiment.

Dressing components are suitably stored prior to use in sterile, sealed, water-impervious packages, e.g. dual chamber plastic tubes or laminated aluminium foil packages.

In use, the dressing component or components are removed from their packaging and located in appropriate order on the skin of a human or animal, e.g. over a wound or other region of skin to be treated for cosmetic or therapeutic purposes. The dressing may also be used as an adjuvant for transdermal delivery, as noted above. The dressing is activated, in the case of multiple component dressings, by bringing the components into contact, resulting in release from the dressing of one or more S-nitrosothiols (after generation in the dressing after activation). S-nitrosothiols decompose spontaneously to produce nitric oxide, which has beneficial effects on tissues and also causes vasodilation.

Skin dressings, and related compositions and methods, may be further understood with reference to the following illustrative, non-exclusive examples.

EXAMPLES

Materials and Methods

Chemicals & Other Materials
Water (conductivity<10 $\mu S\ cm^{-1}$; either analytical reagent grade, Fisher or Sanyo Fistreem MultiPure)
Sodium nitrite, from Sigma (S2252)
1-Thioglycerol, from Fluka (88641)
Hydrochloric acid, from Fisher (J/4310/17)
Ferrous sulphate, from Aldrich (21, 542-2)
Cupric nitrate, from Aldrich (467855)
Zinc sulphate, from Sigma (Z4750)
Sodium citrate, from Fisher (BPE327-500)
Measurement of S-Nitrosothiol Concentration in Aqueous Solutions Using Direct Absorbance Measurement at 338 nm Nitrosothiols are known to absorb UV light around 338 nm ($\epsilon_{338}$=approximately 900 $M^{-1}\ cm^{-1}$). The nitrosylation rate can therefore be followed by direct absorbance measurement at 338 nm (Cook et al. Analytical Biochemistry, 238, 150-158, 1996). A solution containing nitrite (5 mM) and a given concentration of transition metal (either $Cu^{2+}$ or $Zn^{2+}$) was prepared in citrate buffer (50 mM, either pH 4.0 or pH 4.5) and absorbance (338 nm) was measured. 1-Thioglycerol was added to the mixture to achieve 5 mM concentration and changes in absorbance (338 nm) were followed as a function of time. Due to interference from iron species this method could not be used when studying the effect of $Fe^{2+}$ cations on the rate of nitrosylation rate.
Measurement of S-Nitrosothiol Concentration in Aqueous Solutions Using the Griess Method This method was used when studying the effect of $Fe^{2+}$ cations on the rate of nitrosylation rate. A solution containing nitrite (5 mM) and a given concentration of $Fe^{2+}$ was prepared in citrate buffer (either pH 4.0 or pH 4.5 or pH 5.0). 1-Thioglycerol was added to the mixture to achieve 5 mM concentration and the concentration of S-nitroso-1-thioglycerol was measured as a function of time using the following procedure (based on Cook et al. Analytical Biochemistry, 238, 150-158, 1996):

The following reagents were prepared:
Reagent 1: Na-phosphate buffer (pH 7.4, 0.1 M)
Reagent 2: Griess reagent: 20 mg of N-(1-Naphthyl)ethylendiamine dihydrochloride (NADD)+500 mg of sulphanilamide dissolved in 2 mL of DMSO. (N.B. This solution is light sensitive and should be kept in the dark as much as possible.)
Reagent 3: Mercuric chloride (10 mM) in DMSO (13.58 mg of $HgCl_2$ in 5 mL of DMSO)
The six-step procedure set out below was then followed:
Dispense 1.5 mL of Reagent 1 into a plastic cuvette.

Add 200 µL of the sample (i.e. sample in which S-nitroso-1-thioglycerol concentration is to be determined).
Add 1.17 mL of DI water.
Add 100 µL of Reagent 2.
Add 30 µL of Reagent 3 and give the solution a good mix. Read absorbance of the resulting mixture at 496 nm in 10 min.

The concentration of nitrosothiol concentration can be estimated from the absorbance reading using the molar absorption coefficient for nitrosothiols=approximately 10,000 $M^{-1}$ $cm^{-1}$.

Example 1

Effect of $Cu^{2+}$ on the Rate of Nitrosylation of 1-Thioglycerol

Figure 2:
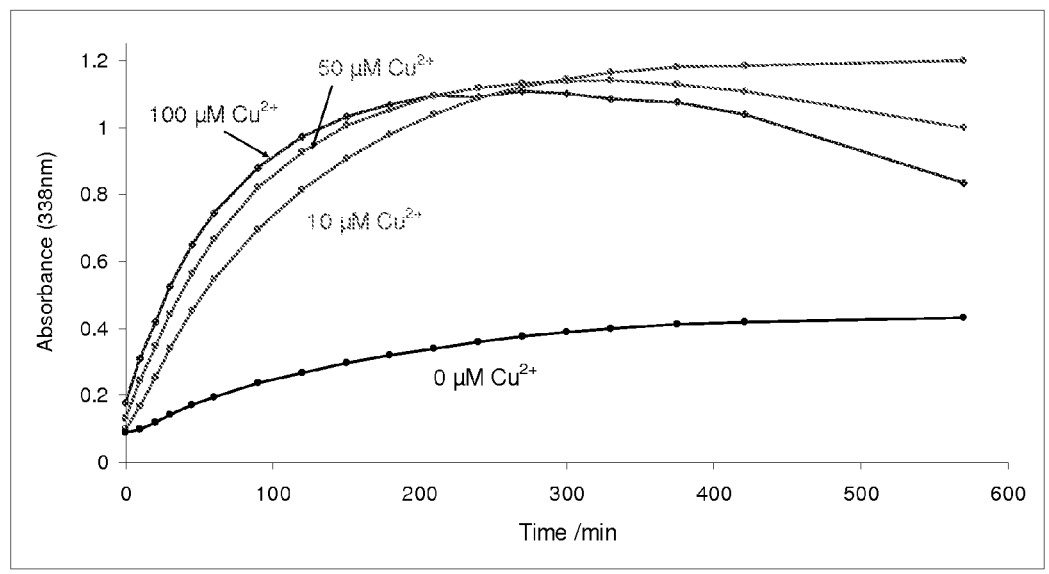
FIG. 2 is a graph of absorbance (338 nm) versus time (in minutes) showing the effect of cupric cations on the rate of nitrosylation of 1-thioglycerol at pH 4.5. The absorbance (338 nm) is directly proportional to the concentration of S-nitroso-1-thioglycerol in the solution.
Figure 3:
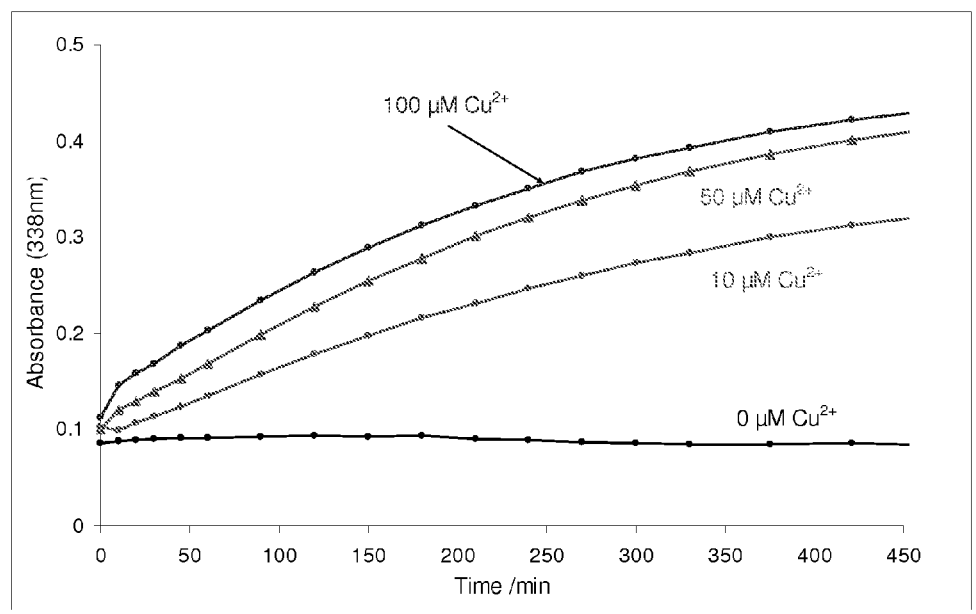
FIG. 3 is a graph of absorbance (338 nm) versus time (in minutes) showing the effect of cupric cations on the rate of nitrosylation of 1-thioglycerol at pH 5.0. The absorbance (338 nm) is directly proportional to the concentration of S-nitroso-1-thioglycerol in the solution.

This example demonstrates the effect of cupric cations on the rate of nitrosothiol generation at pH 4.0 (FIG. 1), pH 4.5 (FIG. 2) and pH 5.0 (FIG. 3). The rate of nitrosylation, followed by measuring absorbance of the samples at 338 nm, increased considerably in the presence of cupric cations in the concentration range 10 µM to 100 µM.

Example 2

Effect of $Zn^{2+}$ on the Rate of Nitrosylation of 1-Thioglycerol

Figure 4:
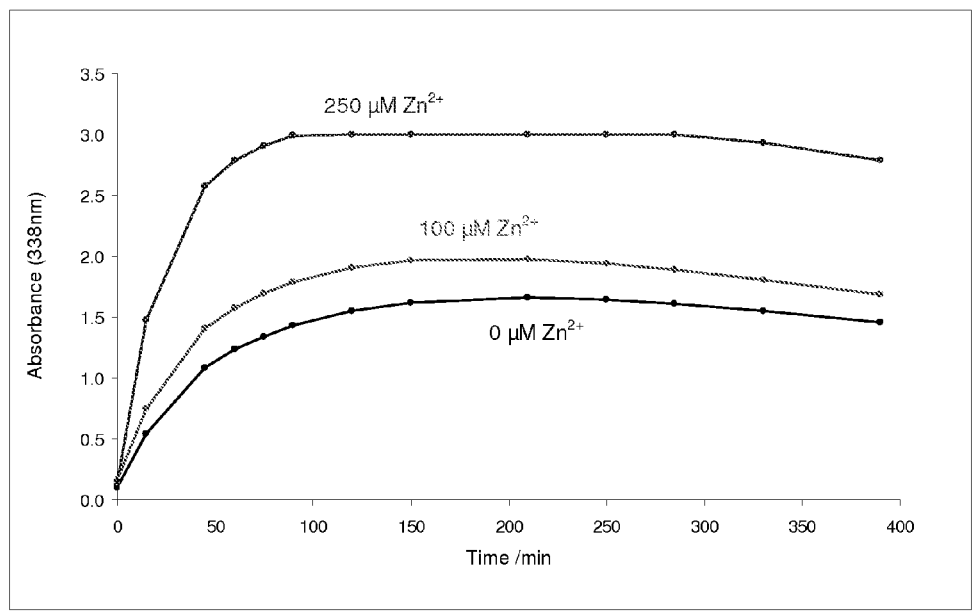
FIG. 4 is a graph of absorbance (338 nm) versus time (in minutes) showing the effect of zinc cations on the rate of nitrosylation of 1-thioglycerol at pH 4.0. The absorbance (338 nm) is directly proportional to the concentration of S-nitroso-1-thioglycerol in the solution.

This example demonstrates the effect of zinc cations on the rate of nitrosothiol generation at pH 4.0 (FIG. 4). The rate of nitrosylation, followed by measuring absorbance of the samples at 338 nm, increased in the presence of 100 µM zinc cations. The increase in nitrosylation rate was more marked in the presence of 250 µM zinc cations.

Example 3

Effect of $Fe^{2+}$ on the Rate of Nitrosylation of 1-Thioglycerol

Figure 5:
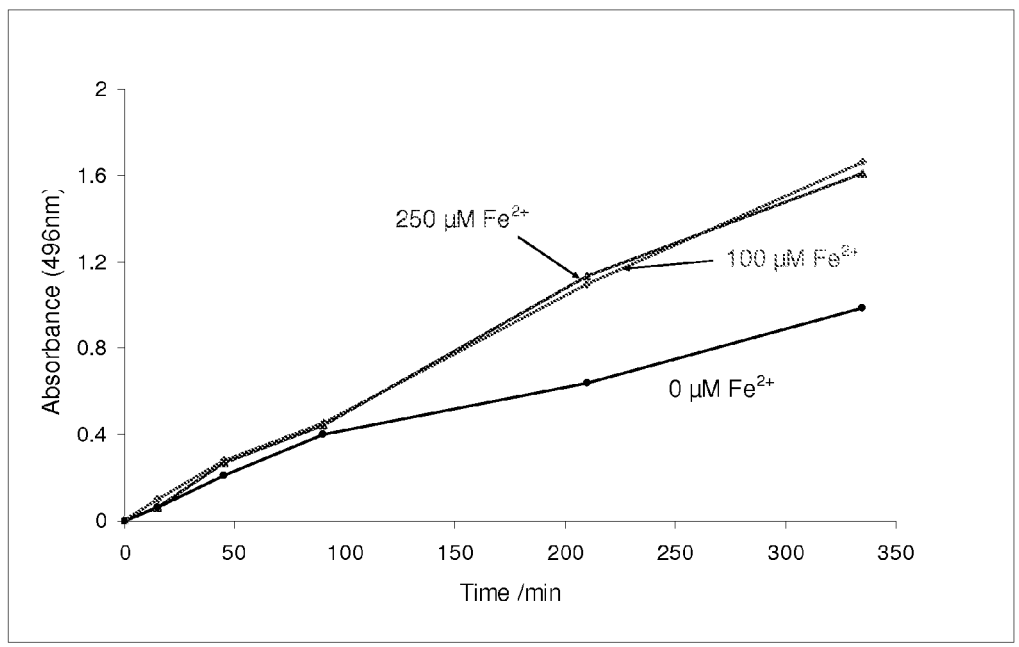
FIG. 5 is a graph of absorbance (496 nm) versus time (in minutes) showing the effect of ferrous cations on the rate of nitrosylation of 1-thioglycerol at pH 4.0. The absorbance (496 nm) is directly proportional to the concentration of S-nitroso-1-thioglycerol in the solution.
Figure 6:
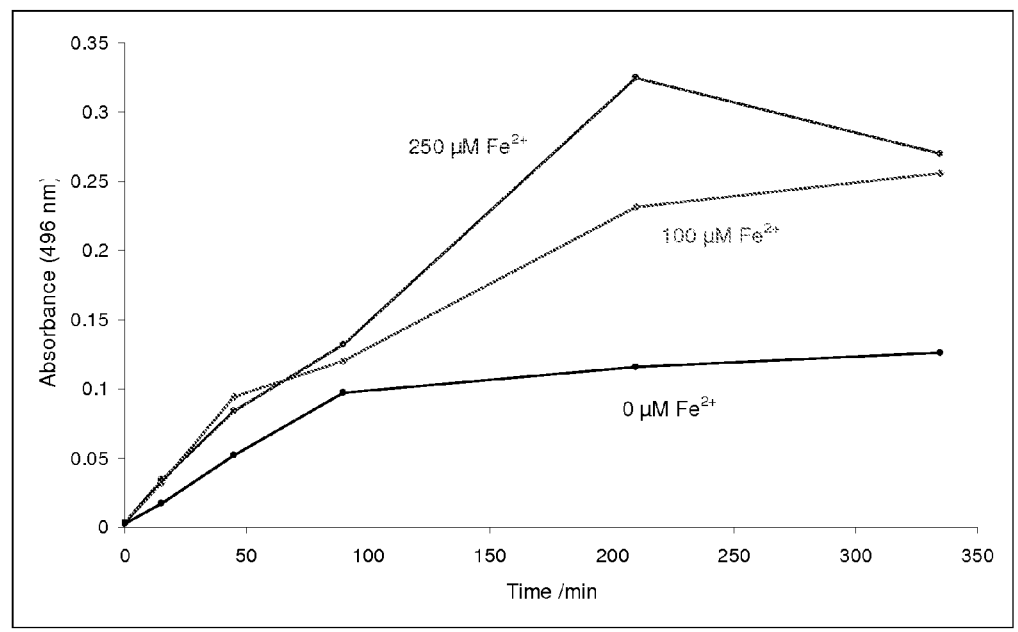
FIG. 6 is a graph of absorbance (496 nm) versus time (in minutes) showing the effect of ferrous cations on the rate of nitrosylation of 1-thioglycerol at pH 4.5. The absorbance (496 nm) is directly proportional to the concentration of S-nitroso-1-thioglycerol in the solution.

This example demonstrates the effect of ferrous cations on the rate of nitrosothiol generation at pH 4.0 (FIG. 5) and pH 4.5 (FIG. 6). The rate of nitrosylation could not be followed by measuring absorbance of the samples at 338 nm due to interference from the iron species. Instead, the generation of the S-nitroso-1-thioglycerol was followed by the Griess method (Cook et al. Analytical Biochemistry, 238, 150-158, 1996). The nitrosylation rate was found to increase in the presence of both 100 µM and 250 µM ferrous cations.

The invention claimed:

1. A skin dressing adapted, on activation, to generate one or more S-nitrosothiols by reaction between a thiol and a nitrite salt in the skin dressing, the skin dressing comprising:
   a first component comprising the nitrite salt and a buffer with a $pK_a$ of from 4.5 to 7.0;
   a second component comprising the thiol, wherein the second component is kept apart from the first component until activation; and
   a source of $Cu^{2+}$, $Zn^{2+}$ and/or $Fe^{2+}$ ions;
   wherein the only component in the dressing that has a $pK_a$ of from 1.0 to 4.0 is the nitrite, and wherein the thiol is selected from the group consisting of 1-thioglycerol, 1-thioglucose, methyl-ester of cysteine, ethyl-ester of cysteine, glutathione, L-glutathione, cysteine, N-acetyl-cysteine, mercaptoethylamine, and 3-mercaptopropanoic acid.

2. The skin dressing of claim 1, wherein the buffer has a $pK_a$ of from 5 to 6.

3. The skin dressing of claim 1, wherein a pH of the first component is from 2 to 5.

4. The skin dressing of claim 1, wherein a pH of the first component is from 3 to 4.

5. The skin dressing of claim 1, wherein a pH of the second component is from 7 to 10.

6. The skin dressing of claim 5, wherein a pH of the first component is from 3 to 4.

7. The skin dressing of claim 6, wherein the buffer has a $pK_a$ of from 5 to 6.

8. The skin dressing of claim 1, wherein the first and second components are amorphous.

9. The skin dressing of claim 1, wherein the first component and/or the second component comprise a polymeric support.

10. The skin dressing of claim 9, wherein the polymeric support comprises polyacrylic acid.

11. The skin dressing of claim 1, wherein the first component comprises the source of $Cu^{2+}$, $Zn^{2+}$ and/or $Fe^{2+}$ ions.

12. The skin dressing of claim 1, wherein the nitrite salt includes at least one nitrite selected from the group consisting of sodium nitrite and potassium nitrite.

13. A skin dressing comprising:
   a first component including a nitrite salt;
   a second component including a thiol; and
   a source of $Cu^{2+}$, $Zn^{2+}$ and/or $Fe^{2+}$ ions;
   wherein the skin dressing has a storage state in which the first component and the second component are separated, and an activated state in which the first component and the second component contact one another;
   wherein the skin dressing is adapted, in the activated state, to generate one or more S-nitrosothiols by reaction between the nitrite salt of the first component and the thiol of the second component; and
   wherein the only component in the dressing that has a $pK_a$ of from 1.0 to 4.0 is the nitrite, and wherein the thiol is selected from the group consisting of 1-thioglycerol, 1-thioglucose, methyl-ester of cysteine, ethyl-ester of cysteine, glutathione, L-glutathione, cysteine, N-acetyl-cysteine, mercaptoethylamine, and 3-mercaptopropanoic acid.

14. The skin dressing of claim 13, wherein the first component includes a buffer with a $pK_a$ of from 4.5 to 7.0.

15. The skin dressing of claim 13, wherein at least one of the first component and the second component includes the source of $Cu^{2+}$, $Zn^{2+}$ and/or $Fe^{2+}$ ions.

* * * * *